United States Patent [19]

Nelson

[11] 3,968,144

[45] July 6, 1976

[54] 5-OXA-11-DEOXY PHENYL- AND PHENOXY-SUBSTITUTED PROSTAGLANDIN $E_1$ ANALOGS

[75] Inventor: Norman A. Nelson, Galesburg, Mich.

[73] Assignee: The Upjohn Company, Kalamazoo, Mich.

[22] Filed: Nov. 18, 1974

[21] Appl. No.: 524,959

Related U.S. Application Data

[62] Division of Ser. No. 361,990, May 21, 1973, Pat. No. 3,864,387.

[52] U.S. Cl. .......................... 260/473 A; 260/520 B
[51] Int. Cl.² .......................................... C07C 69/76
[58] Field of Search ...................... 260/473 A, 520

[56] References Cited

FOREIGN PATENTS OR APPLICATIONS

| | | |
|---|---|---|
| 2,165,184 | 7/1972 | Germany |
| 2,154,309 | 5/1972 | Germany |
| 7,118,204 | 7/1972 | Netherlands |
| 7,206,361 | 11/1972 | Netherlands |

*Primary Examiner*—Paul J. Killos
*Attorney, Agent, or Firm*—Morris L. Nielsen

[57] ABSTRACT

5-Oxa-11-deoxy phenyl- and phenoxy-substituted prostaglandin type compounds and processes for making them. These compounds are useful for a variety of pharmacological purposes, including anti-ulcer, inhibition of platelet aggregation, increase of nasal patency, labor inducement at term, and wound healing.

17 Claims, No Drawings

5-OXA-11-DEOXY PHENYL- AND PHENOXY-SUBSTITUTED PROSTALANDIN $E_1$ ANALOGS

CROSS REFERENCE TO RELATED APPLICATIONS

This application is a divisional of my co-pending application Ser. No. 361,990 filed May 21, 1973 now issued as U.S. Pat. No. 3,864,387.

BACKGROUND OF THE INVENTION

This invention relates to novel compositions of matter, to novel methods for producing those, and to novel chemical intermediates useful in those processes. Particularly, this invention relates to certain novel analogs of prostaglandins $E_1$, $F_{1\alpha}$, $F_{1\beta}$, $A_1$, and $B_1$ in which the C-5 methylene ($-CH_2$) in the prostanoic acid structure is replaced by oxygen ($-O-$).

The essential material for this application, including the background of the invention, the disclosure of the invention, and the description of the preferred embodiments, including Preparations and Examples, is incorporated by reference from U.S. Pat. No. 3,864,387, columns 1–89 inclusive, under the provisions of M.P.E.P. 608.01(p).

SUMMARY OF THE INVENTION

It is a purpose of this invention to provide novel 5-oxa prostagalandin E, F, A, and B analogs. It is a further purpose to provide novel 5-oxa prostaglandin analogs with a variety of substituents and degrees of saturation in the side chains. It is a further purpose to provide 5-oxa prostaglandin analogs having the 11-deoxy ring-structure in which the 11-hydroxy is replaced by hydrogen. It is a further purpose to provide esters, lower alkanoates, and pharmacologically acceptable salts of said analogs. It is a further purpose to provide novel processes for preparing said analogs and esters. It is still a further purpose to provide novel intermediates useful in said processes.

The novel prostaglandin analogs of this invention each have an oxygen ($-O-$) in place of the methylene ($-CH_2-$) moiety at the 5-position of the prostanoic acid formula. They are represented by the generic formula

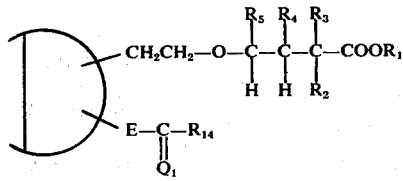   VII wherein D is one of the six carbocyclic moieties:

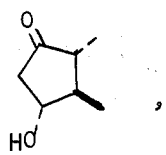 , 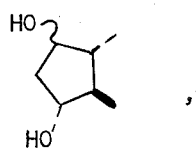 , 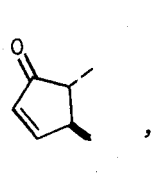 ,

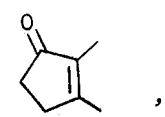 , 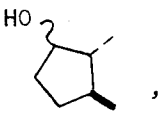 , or 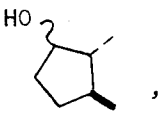 , wherein ~ indicates alpha or beta attachment of hydroxyl to the cyclopentane ring; wherein E is $-CH_2CH_2-$ or

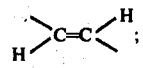 ;

wherein $Q_1$ is

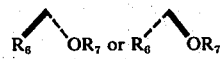

wherein $R_6$ and $R_7$ are hydrogen or alkyl of one to 4 carbon atoms, inclusive, being the same or different; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein $R_3$ is hydrogen, alkyl of one to 4 carbon atoms, inclusive, or fluoro; wherein $R_2$ is hydrogen or fluoro, with the proviso that $R_2$ is fluoro only when $R_3$ is hydrogen or fluoro; wherein $R_4$ and $R_5$ are hydrogen or alkyl of one to 4 carbon atoms, inclusive, being the same or different with the proviso that no more than one of $R_3$, $R_4$, and $R_5$ is alkyl; and wherein $R_{14}$ is

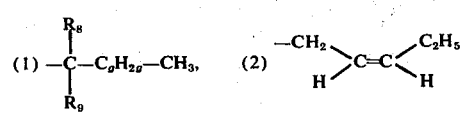

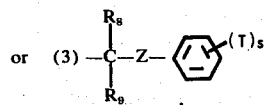

with the proviso that $R_{14}$ is

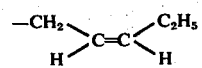

only when E is

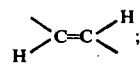 ;

wherein $C_gH_{2g}$ is alkylene of one to 9 carbon atoms, inclusive, with one to 5 carbon atoms, inclusive, in the chain between -CR₈R₉- and terminal methyl; wherein R₈ and R₉ are hydrogen, alkyl of one to 4 carbon atoms, inclusive, or fluoro, being the same or different, with the proviso that R₉ is fluoro only when R₈ is hydrogen or fluoro; wherein T is alkyl of one to 4 carbon atoms, inclusive, fluoro, chloro, trifluoromethyl, or —OR₁₀, wherein R₁₀ is hydrogen or alkyl of one to 4 carbon atoms, inclusive, and s is zero, one, 2, or 3, with the proviso that not more than two T's are other than alkyl; and wherein Z represents an oxa atom (—O—) or C$_j$H$_{2j}$, wherein C$_j$H$_{2j}$ is a valence bond or alkylene of one to 9 carbon atoms, inclusive, substituted with zero, one, or 2 fluoro, with one to 6 carbon atoms, inclusive, between —CR₈R₉— and the ring.

The presently described acids and esters of the 5-oxa prostaglandin analogs include compounds of the following formulas which are intended to represent the same optically form as of the naturally occurring prostaglandins. There are also included the racemic compounds represented by each respective formula and the mirror image thereof. There are also included the alkanoates of two to 8 carbon atoms, inclusive and also the pharmacologically acceptable salts thereof when R₁ is hydrogen.

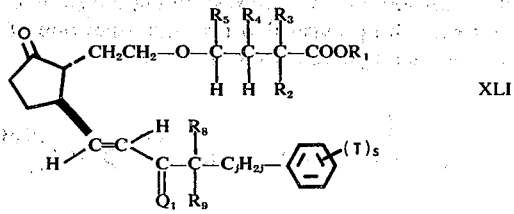

XLI

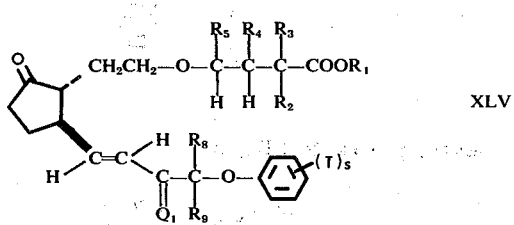

XLV

I claim:
1. An optically active compound of the formula

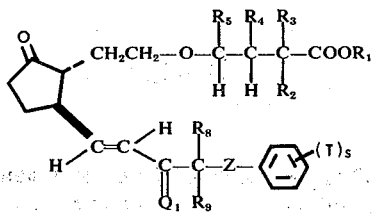

or a racemic compound of that formula and the mirror image thereof, wherein Z represents an oxa atom (—O—) or C$_j$H$_{2j}$ wherein C$_j$H$_{2j}$ is a valence bond or alkylene of one to 9 carbon atoms, inclusive, substituted with zero, one, or 2 fluoro, with one to 6 carbon atoms, inclusive, between —CR₈R₉— and the ring; wherein T is alkyl of one to 4 carbon atoms, inclusive, fluoro, chloro, trifluoromethyl, or —OR₁₀, wherein R₁₀ is hydrogen or alkyl of one to 4 carbon atoms, inclusive, and s is zero, one, 2, or 3, with the proviso that not more than two T's are other than alkyl and when s is 2 or 3 the T's are either the same or different; wherein Q₁ is

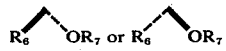

wherein R₆ and R₇ are hydrogen or alkyl of one to 4 carbon atoms, inclusive, being the same or different; wherein R₁ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein when Z is oxa (—O—), R₈ and R₉ are hydrogen or alkyl of one to 4 carbon atoms, being the same or different, and, when Z is C$_j$H$_{2j}$, R₈ and R₉ are hydrogen, alkyl of one to 4 carbon atoms, inclusive, or fluoro, being the same or different, with the proviso that R₉ is fluoro only when R₈ is hydrogen or fluoro; wherein R₃ is hydrogen, alkyl of one to 4 carbon atoms, inclusive, or fluoro; wherein R₂ is hydrogen or fluoro, with the proviso that R₂ is fluoro only when R₃ is hydrogen or fluoro; and wherein R₄ and R₅ are hydrogen or alkyl of one to 4 carbon atoms, inclusive, being the same or different, with the proviso that no more than one of R₃, R₄, and R₅ is alkyl; including the lower alkanoates thereof, and the pharmacologically acceptable salts thereof when R₁ is hydrogen.

2. A compound according to claim 1 wherein Q₁ is

wherein R₆ and R₇ are hydrogen or alkyl of one to 4 carbon atoms, inclusive, being the same or different.

3. A compound according to claim 2 wherein the sum of the carbon atoms in R₆, R₇, R₈, and R₉ taken together is not greater than 7.

4. A compound according to claim 3 wherein R₃, R₄, and R₅ are either hydrogen or methyl, and one of R₃, R₄, and R₅ is methyl.

5. A compound according to claim 3 wherein R₂, R₃, R₄, and R₅ are hydrogen.

6. A compound according to claim 5 wherein R₆, R₇, R₈, and R₉ are either hydrogen or methyl, and at least one of R₆, R₇, R₈, and R₉ is methyl.

7. A compound according to claim 6 wherein R₆ is methyl.

8. A compound according to claim 6 wherein R₇ is methyl.

9. A compound according to claim 6 wherein one or both of R₈ and R₉ are methyl.

10. A compound according to claim 5 wherein R₆, R₇, R₈, and R₉ are hydrogen.

11. A compound according to claim 10 wherein Z is oxa (—O—).

12. 5-Oxa-11-deoxy-16-phenoxy-17,18,19,20-tetranor - PGE₁, methyl ester, a compound according to claim 11.

13. A compound according to claim 10 wherein Z is methylene.

14. An optically active compound according to claim 13.

15. A compound according to claim 14 wherein R₁ is alkyl of one to 12 carbon atoms, inclusive.

16. 5-Oxa-11-deoxy-17-phenyl-18,19,20-trinor - PGE₁, methyl ester, a compound according to claim 15.

17. A compound according to claim 14 wherein R₁ is hydrogen.

* * * * *